United States Patent [19]
McNaughton

[11] Patent Number: 5,928,143
[45] Date of Patent: Jul. 27, 1999

[54] IMPLANTABLE MULTI-ELECTRODE MICRODRIVE ARRAY

[75] Inventor: Bruce L. McNaughton, Tucson, Ariz.

[73] Assignee: Arizona Board of Regents on Behalf of The University of Arizona, Tucson, Ariz.

[21] Appl. No.: 08/822,604

[22] Filed: Mar. 19, 1997

Related U.S. Application Data

[60] Provisional application No. 60/014,124, Mar. 29, 1996.

[51] Int. Cl.$^6$ ........................................... A61B 5/04
[52] U.S. Cl. ..................... 600/373; 600/378; 600/544; 606/130
[58] Field of Search ..................... 600/373, 377, 600/378, 393, 544, 417, 429; 607/116, 127, 139; 606/130, 41, 129, 11; 604/27, 156, 164

[56] References Cited

U.S. PATENT DOCUMENTS

| | | | |
|---|---|---|---|
| 3,089,483 | 5/1963 | Sheatz | 600/377 |
| 3,841,310 | 10/1974 | Goldstein . | |
| 4,620,540 | 11/1986 | Goodale . | |
| 4,632,122 | 12/1986 | Johansson et al. | 600/544 |
| 5,237,996 | 8/1993 | Waldman et al. . | |
| 5,357,957 | 10/1994 | Itil et al. | 600/544 |
| 5,413,103 | 5/1995 | Eckhorn . | |
| 5,607,462 | 3/1997 | Imran | 607/122 |
| 5,788,713 | 8/1998 | Dubach et al. | 606/130 |

FOREIGN PATENT DOCUMENTS

0753284 A2  1/1997  European Pat. Off. .

OTHER PUBLICATIONS

M. Saburi et al "A Multielectrode System Composed of Independent Glass Micropipettes with an Excentric Tip Structure for Simultaneous Intracellular Tecording" IEEE Transactions on BME, vol. 39, No. 6, Jun. 1992, New York, pp. 656–658.

R.P. Vertes "A device for recording single unit activity in freely–moving rats by a movable fine–wire microelectrode" *Electroencephalography and Clinical Neurophysiology*, vol. 38, No. 1, Jan 1975, pp. 90–92.

J.L. Ckydell et al "A Chronic electrode implantation technique for sub–mammalian vertebrates" *Electroencephalography and Clinical Neurophysiology*, vol. 38, No. 3, Mar. 1975, pp. 325–328.

Deadwyler et al, "A Microdrive for Use with Glass or Metal Microelectrodes in recording from Freely–Moving Rats," *Electroencephalography and Clinical Neurophysiology*, 1979, 47: 752–754.

Hampson et al, "Hippocampal Place Fields: Relationship Between Degree of Field Overlap and Cross–Correlations Within Ensembles of Hippocampal Neurons," published in *Hippocampus*, 1996, 6:281–293.

*Primary Examiner*—Danton D. DeMille
*Assistant Examiner*—David M. Ruddy
*Attorney, Agent, or Firm*—Bruce H. Johnsonbaugh

[57] ABSTRACT

An apparatus is provided for use in neurophysiological research in general, and, in particular, for use on conscious, freely moving animals and on in vitro tissue samples. An array of elongated guide cannulae have lower ends which are parallel with and adjacent each other and upper ends which are inclined outwardly. Recording electrodes are slidably carried within each of the guide cannulae and an electrode adjustment mechanism moves the electrode or electrodes in each of the guide cannulae independently of the electrodes carried in the other guide cannulae. The apparatus has a capacity for recording vastly more timing patterns of neural activity than prior art devices.

7 Claims, 5 Drawing Sheets

IMPLANTABLE MULTI-ELECTRODE MICRODRIVE ARRAY

CROSS-REFERENCE TO RELATED APPLICATION

This application claims the benefit of U.S. Provisional Application No. 60/014,124, filed Mar. 29, 1996.

CONTRACTUAL ORIGIN OF THE INVENTION

The United States Government has rights in this invention under Contract No. N00014-94-1-0154 between the Office of Naval Research and The University of Arizona.

BACKGROUND AND BRIEF SUMMARY OF THE INVENTION

The present invention relates in general terms to brain research instrumentation. More particularly, the present invention provides brain research instrumentation including an array of implantable independently adjustable electrodes capable of, but not limited to, recording from freely moving animals. The invention may also be used for in vitro neurophysiological research wherein tissue slices are investigated. It may also be used to perform neurophysiological research on humans. Potential future uses of the invention include clinical diagnostic uses in both humans and animals.

Prior art brain research instrumentation includes movable single channel or single electrode mechanisms which were limited to recording from single locations in the brain. Early research tended to be concentrated in sensory portions of the brain such as the visual cortex. For example, the research would seek to identify what particular stimulus in the subject's visual field would cause an individual neuron in the visual cortex to fire. The prior art single electrode mechanisms were capable of being moved to different locations in the brain but were only capable of recording from a single neuron or a small neuron cluster at a time.

The prior art also includes apparatus with multiple electrodes whose position in space is fixed relative to the other electrodes. These prior art electrodes are capable of recording timing or firing patterns of multiple neurons or multiple small clusters of neurons. The importance of being able to record timing patterns is critical to understanding higher order functions of the brain. However, the multi-channel or multi-electrode prior art devices could only be used in restrained animal subjects and were not capable of being moved within the brain. Thus, the timing patterns that could be recorded within the brain were limited by the number of electrodes and to only those patterns that occurred between the individual neurons or small neuron clusters that happen to be near the tips of the recording electrodes. Another disadvantage of the fixed array of electrodes is that the research is inherently limited to those brain functions performed by a non-moving subject.

The present invention provides four significant improvements over the prior art. First, the present invention provides an increased number of recording electrodes, capable of recording a much larger combination of timing patterns. Secondly, the present invention provides electrodes which are independently adjustable, further increasing the number of recordable timing patterns by improving the "yield" or effectiveness of each electrode, as well as increasing the combinations of regions within the brain that may be examined in a given experiment. Thirdly, the present invention is small enough and lightweight enough to be easily carried on the skull of the subject animal and this allows for study of activities which involve free motion of the subject, for example, navigational skills and spatial orientation skills. The invention is not limited to use on freely moving subjects; it may be used on unconscious or restrained subjects, and may be used on in vitro tissue samples to study virtually any human or animal brain function. Fourth, the present invention enables the use of much fewer laboratory animals to gather the same amount of research data.

The increased number of electrodes vastly enlarges the capacity of the instrument to record timing patterns. For example, to measure timing patterns of the firing of two neurons, two single electrodes are necessary. As the number of recording electrodes increases, their capacity for recording timing patterns (i.e. sequential firing patterns of neurons) increases dramatically. In fact, if we assume that each electrode is recording effectively and recording independently of other electrodes in the array, it is believed that the increase in the number of timing patterns recordable increases with the factorial of the number of electrodes. For example, in the embodiment of the present invention with 48 separate recording electrodes, the number of timing patterns recordable (assuming each electrode records one neuron) would be 48 factorial (48!). To illustrate the theoretical capacity of the present invention, 48 factorial (48!) is approximately $1.24 \times 10^{61}$ possible recordable and distinct firing patterns, whereas a prior art device with 20 stationary electrodes has a theoretical capacity of recording 20 factorial (20!) or approximately $2.43 \times 10^{18}$ distinct, recordable firing patterns. The present invention has a capacity approximately $5.1 \times 10^{42}$ times greater than the prior art, a gigantic step forward in trying to unravel the mystery of higher order brain functions.

A related advantage of a larger number of electrodes is the pairwise interaction, which increases as $n^2$ where n is the number of electrodes.

Another advantage of the present invention is that, by independently moving the electrodes, we are capable of locating the recording tips at points of interest and increasing the "yield" of each electrode. By properly locating the electrodes, we can obtain a yield of useful recording from as many as 150 neurons with 48 electrodes. This can be accomplished by properly locating electrodes and identifying firing patterns of neurons between electrodes. In contrast, the prior art device using 20 non-movable electrodes typically has a yield of 10 to 15 neurons because the recording tips are not movable relative to each other and the array of 20 electrodes is not movable within the brain. The increased yield obtained by the present invention further increases the capacity of recording timing patterns.

It is believed that the present invention may in the future lead to an understanding of the learning process, diagnosis of learning disorders, possible spinal damage bypass (or "neural prosthesis") development, and various clinical diagnostic possibilities for both animals and humans.

Accordingly, a primary object of the present invention is to provide an implantable adjustable multi-electrode microdrive array capable of recording vastly more timing patterns of neural firing than recordable by devices of the prior art.

A further object of the invention is to provide a brain research instrument having an array of electrodes wherein the recording electrodes are independently adjustable.

Another object of the invention is to provide a neurophysiological research instrument with a yield greater than one, i.e., n electrodes are capable of recording as many as 3n neurons.

A further object of the invention is to provide a device for neurological research in animal subjects in which a much smaller number of subjects is needed in order to generate the same research data as would be required by using prior art devices.

A further object of the invention is to provide a device for neurophysiological research in conscious animal subjects wherein the animal subjects may move about freely.

A further object of the invention is to provide a device for neurophysiological research capable of investigating navigational and motion related brain activities, and related learning processes, which simply cannot be investigated in a restrained or unconscious subject.

Other objects and advantages of the invention will become apparent from the following description and the drawings wherein:

DETAILED DESCRIPTION OF THE DRAWINGS

Figure 1:
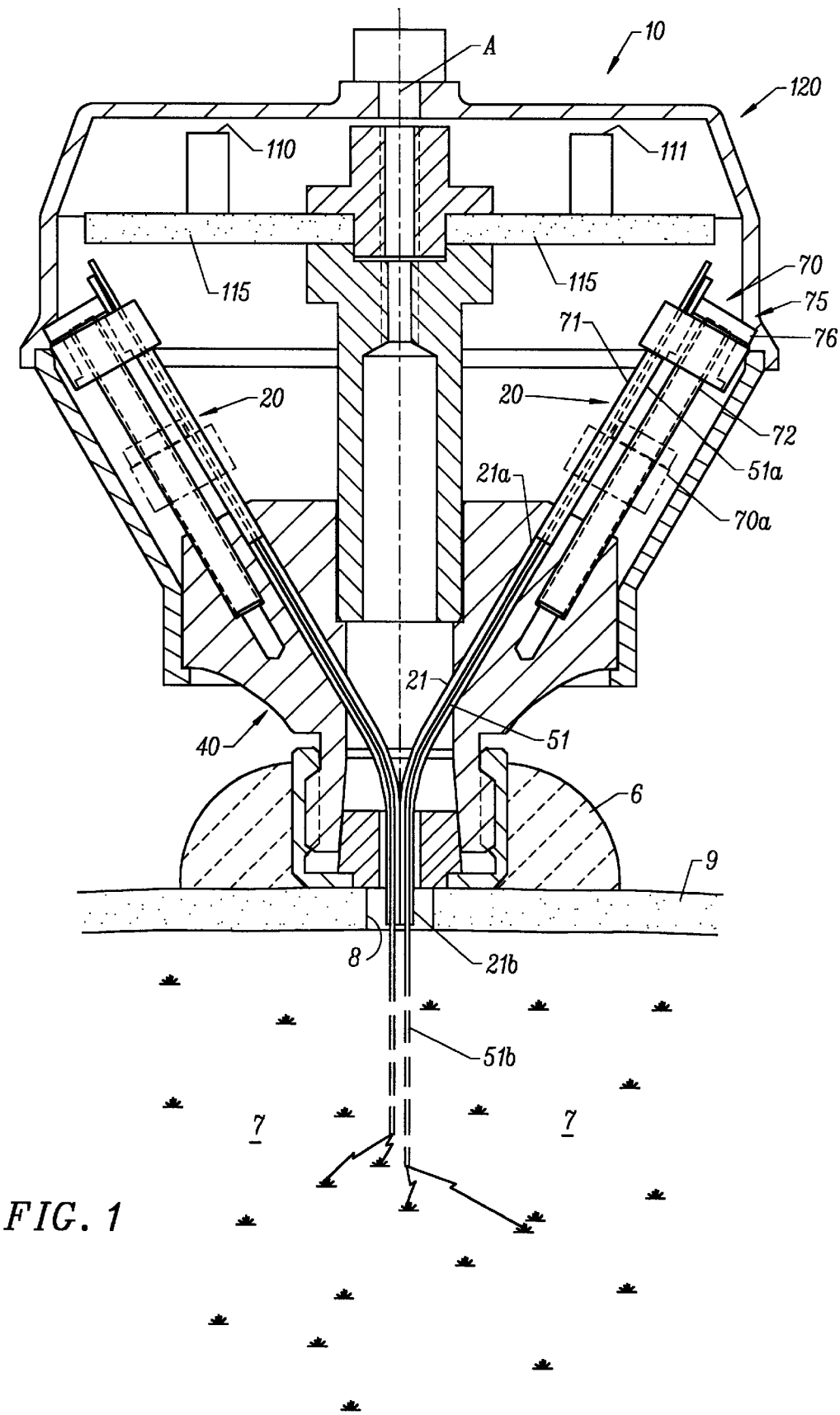
FIG. 1 is a sectional view of the apparatus according to the present invention shown schematically as attached to the skull of a freely moving animal subject.

As shown best in FIG. 1, the apparatus referred to generally as 10 of the present invention is shown mounted on the skull 9 of a subject animal such as a rat. The apparatus is relatively small and lightweight, for example, being approximately 1½ inches in diameter and approximately 1¾ inches high and weighing approximately 23 grams. It is sufficiently small and lightweight that it may be implanted on animals as small as rats and the subject animals tolerate the apparatus and are able to move freely with the apparatus in place.

The apparatus includes an array of elongated guide cannulae referred to generally as 20 which provide a guide means for the recording electrodes. In the embodiment shown best in FIG. 2, a total number of guide cannulae provided is 14. The 14 cannulae and their associated drive mechanisms are identical. For clarity, only one of the 14 is described in detail. Each of the guide cannulae, such as individual cannula 21 shown in FIG. 1, has an upper end 21a and a lower end 21b. The lower ends of each cannula are aligned parallel with and are adjacent each other. The 14 guide cannulae, shown in the embodiments of FIGS. 1 and 2, easily fit into a small ⅛ inch diameter passageway 8 formed in the skull 9 of the subject animal.

The upper end 21a of cannula 21 is inclined outwardly from the central vertical axis A of the apparatus 10 by preferably an angle of 30°. Other angles may be used. By inclining the upper ends of the array of cannulae 20 outwardly, as shown best in FIG. 2, sufficient spacing is obtained between adjacent cannulae that electrodes carried within the cannulae are capable of being independently adjusted relative to each other.

A support means 40 is provided for the array of guide cannulae 20. The support means is preferably a mechanical plastic core. The plastic core has an upper end 42 and a lower end 43. A first passageway 44 is formed in the lower end 43 of the plastic core, and is adapted to receive a cylindrical bushing 49 with an internal passageway 48 through which the lower ends of the array of guide cannulae 20 extend, as shown best in FIG. 3. The support means or plastic core 40 also has a plurality of inclined passageways such as 46 formed in its upper portion 42 for each upper portion of each guide cannula. Each of the inclined passageways such as 46 communicates with the passageway 48 formed by bushing 49 and extends upwardly and preferably outwardly at an angle of 30° of the vertical axis A. Each of the guide cannulae remains fixed relative to support means 40 with upper end 21a terminating just below the upper surface 42a of support means 40.

Each of said guide cannulae in the array 20 carries one or more electrodes. For example, guide cannula 21 shown in FIG. 1 carries in the preferred embodiment a group of four electrodes 51, which is referred herein as a tetrode. The tetrode 51 has an upper end 51a which is located in the upper portion 21a of guide cannula 21. The tetrode 51 has a lower portion 51b which is capable of being moved downwardly into the brain 7 to various depths.

The preferred electrode assembly includes a tetrode which comprises four recording probes made by twisting together four strands of polyamide-coated, 14 micron diameter, nichrome wire. To obtain adherence and stiffness, the insulation is briefly softened by heating, while the wires are under tension, and then allowed to cool. Wires are cut flat at the same level and each tip is gold-plated separately to reduce the impedance of individual electrodes to 400–500 K-ohm. The overall diameter of each tetrode is approximately 40 microns. The tetrode is mounted and glued into two nested polyamide tubes, those tubes being 78 and 110 microns outside diameter, respectively, which are then mounted in the support means 40. The smaller tubing (78 micron O.D.) forms each guide cannula 21 and the larger tubing (110 micron O.D.) forms each drive cannula 71.

Electrode adjustment means shown generally as 70 (FIG. 1) are connected to the upper end of each electrode and each guide cannula. The electrode adjustment drive means 70 is capable of moving the electrode or electrode bundle in each guide cannula independently of the electrodes carried in the other guide cannulae in the array 20. As shown in FIG. 1, each electrode adjustment means 70 is capable of moving between the position shown in solid lines downwardly to the position shown in phantom as 70a. Electrode adjustment means 70 in the preferred embodiment shown in FIG. 1 includes a drive cannula 71 slidably mounted over the upper end 21a of guide cannula 21, electrode drive means 75, adjustment rod 72 and guide rod 85 described below. Each guide cannula 21 (typically 78 micron O.D.) slidably nests in drive cannula 71 (typically 110 micron O.D.). The top of electrode 51a slides through and is attached to the top of drive cannula 71 by glue. A plurality of adjustment rod means 72 (FIG. 3) are provided, each of which is carried by support means 40 and each of which is mounted parallel to its respective guide cannula 21. Adjustment rod means 72 is preferably an 0.080" headless stainless screw, threaded into support means 40.

Figure 3:
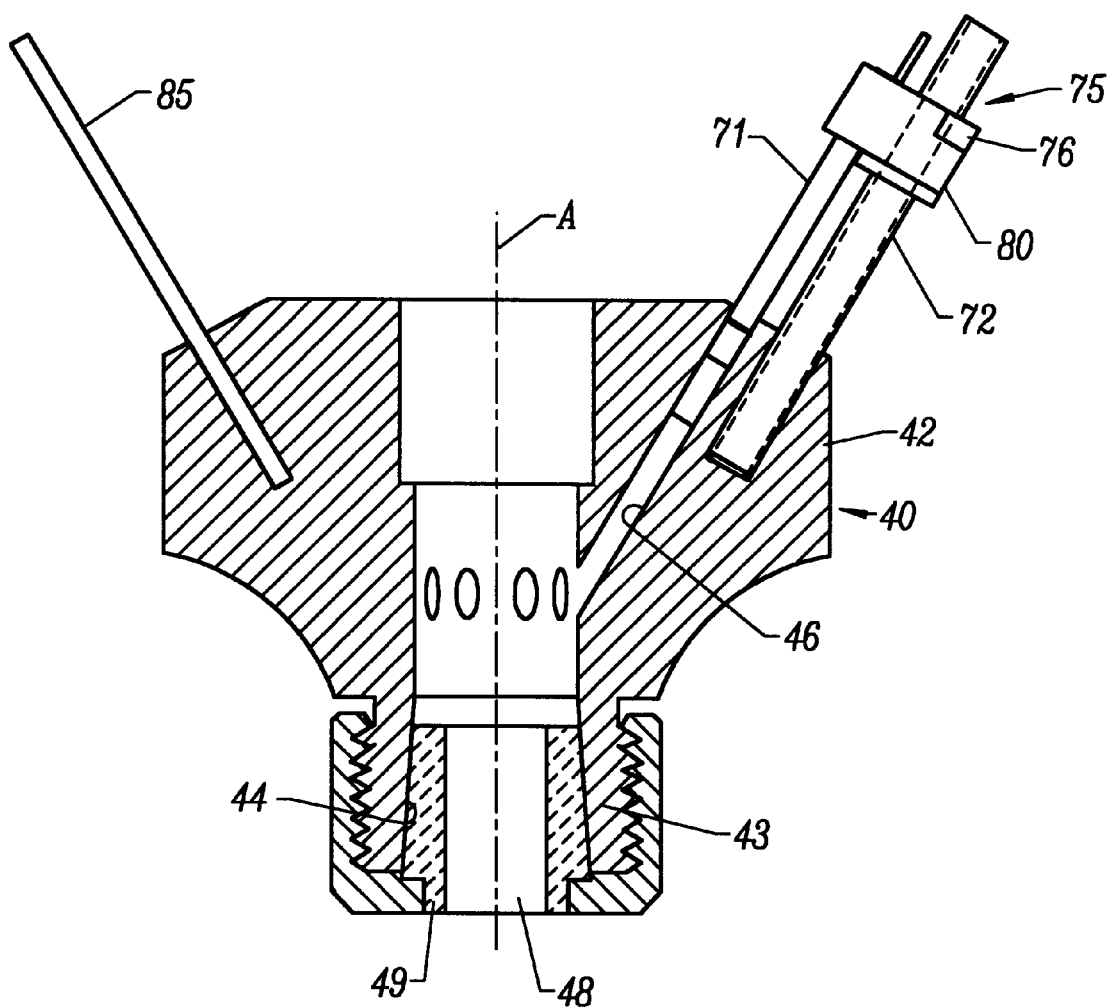
FIG. 3 is a section on the line 3—3 of FIG. 2.
Figure 4A:
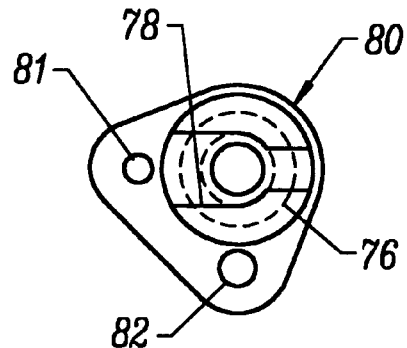
FIG. 4A is a top elevational view of a portion of the electrode adjustment mechanism.
Figure 4B:
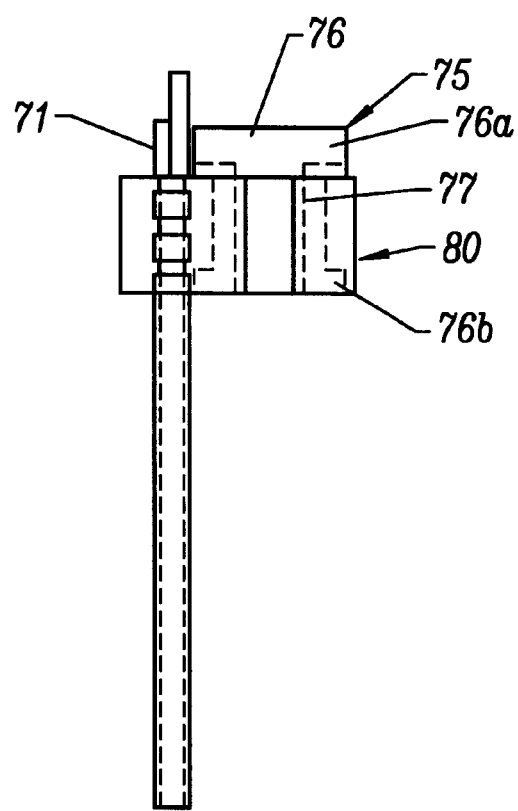
FIG. 4B is a side elevational view of the portion of the electrode adjustment mechanism shown in FIG. 4A.

An electrode drive means 75 is carried by each adjustment rod 72 as shown best in FIG. 3. Electrode drive means 75 includes a cylindrically shaped nut 76 (FIG. 4B) with a threaded inner bore 77 which threads onto threaded rod 72 (FIG. 3). Nut 76 has a turning slot 78 formed in its upper surface.

Figure 2:
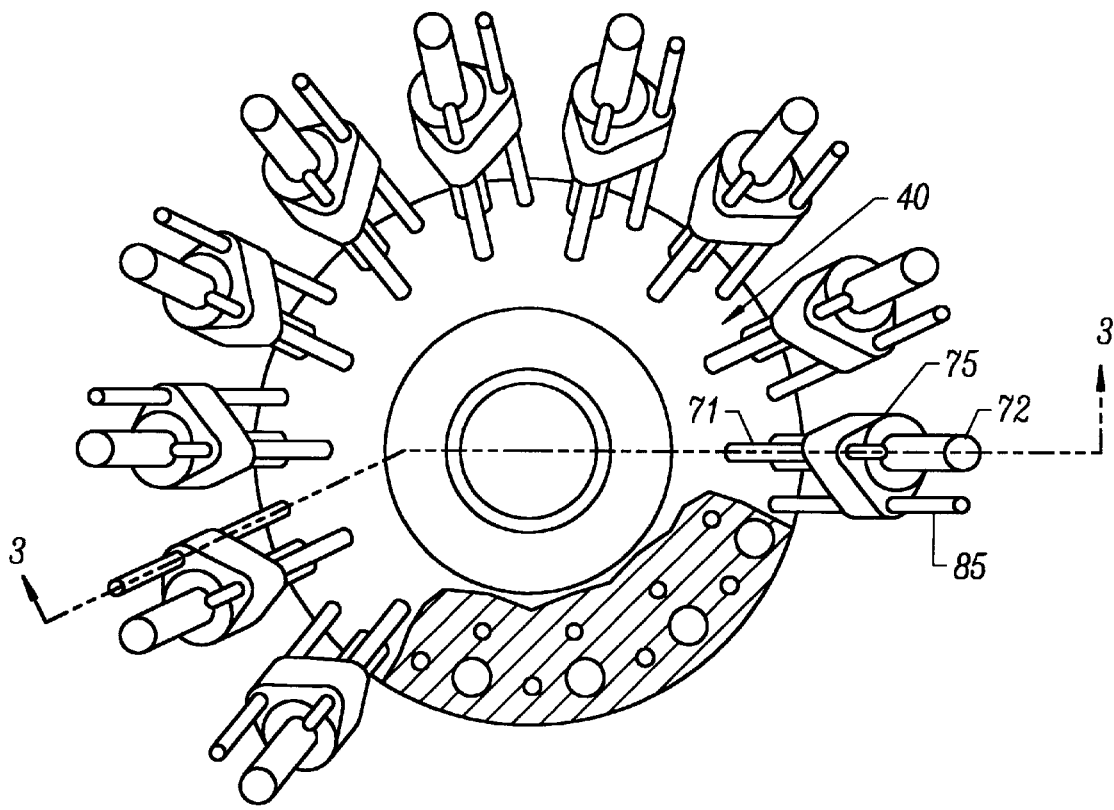
FIG. 2 is a top perspective view showing a portion of the apparatus and showing how the electrode adjustment mechanisms are mounted relative to each other.

Nut 76 is connected to a generally triangular shaped bridge 80. Bridge 80 has a first bore 81 formed therein for carrying drive cannula 71. Nut 76 has an upper flange 76a and a lower flange 76b which cause bridge 80 to move upwardly and downwardly on rod 72 as the nut 76 is turned. Bridge 80 has a second bore 82 formed therein for receiving a guide rod 85 (FIG. 2). Guide rod 85 prevents rotation of bridge 80 relative to adjustment rod 72 as nut 76 is rotated. Guide rod 85 is parallel to adjustment rod 72 and is cemented into support means 40.

Figure 5A:
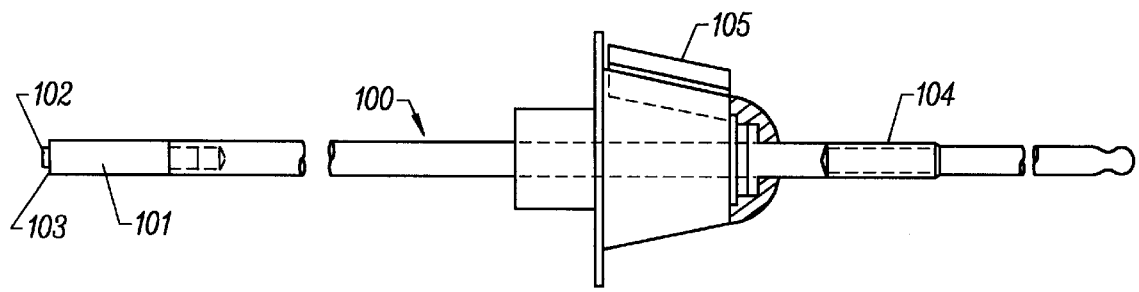
FIG. 5A is a front elevational view of the electrode adjustment tool.
Figure 5B:
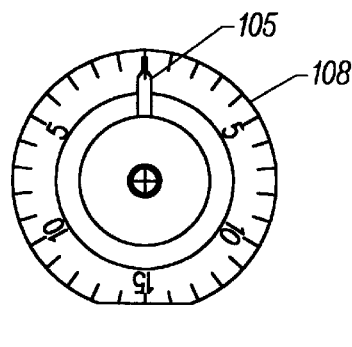
FIG. 5B is a front elevational view of the indicator used on the tool of FIG. 5A.
Figure 5C:
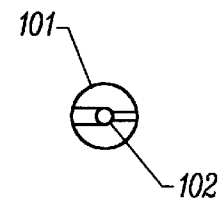
FIG. 5C is a side elevational view showing the tip of the adjustment tool.

An electrode adjustment tool 100 (FIGS. 5A, 5B and 5C)) is provided having a hollow drive sleeve 101 adapted to slide over the top of adjustment rod 72 (FIG. 3). A drive tip 102 is formed at the distal end 103 of sleeve 101. Drive tip 102 engages turning slot 78. A turning knob 105 is carried near the proximal end 104 of sleeve 101 and carries a scale 108 to indicate the motion imparted to an electrode. A full 360° rotation of knob 105 imparts 320 microns axial motion to drive cannula 71 and to the electrode or electrodes 51 carried within that drive cannula.

Figure 6:
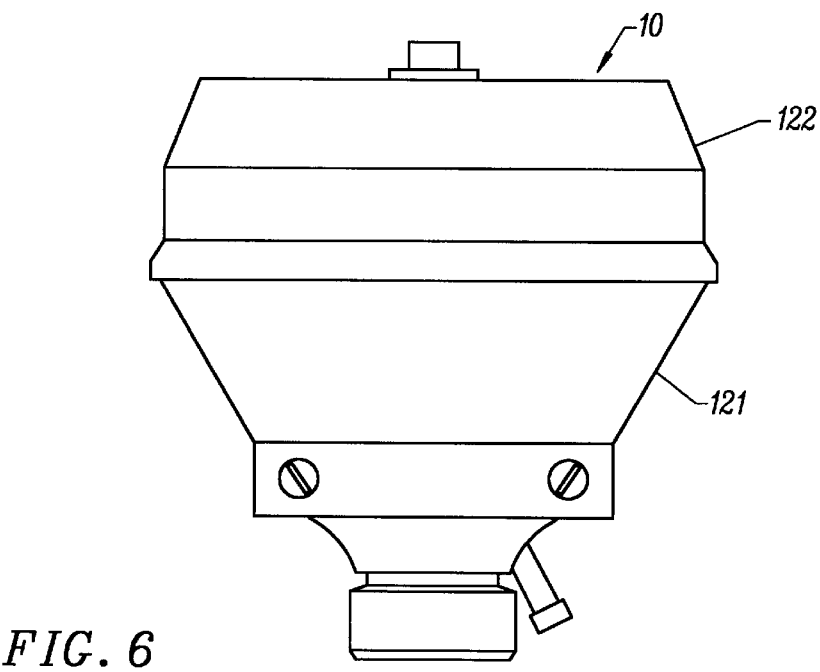
FIG. 6 is a front elevational view of the apparatus with the cover and shroud in place.

The apparatus of the present invention 10 has a cover means 120 including a lower shroud 121 which extends around and encloses the support means 40 and the array of electrode adjustment means and a removable upper cover portion 122 which covers the top of the apparatus when the subject animal is not being recorded (see FIG. 6) and prevents the subject animal from reaching any of the inner components of the apparatus 10. Cover 122 is removed in order to connect the recording electronics to sockets 110 and 111 (FIG. 1).

The apparatus of the present invention has been used to examine rat hippocampus CA1 cells in a spatial navigation task in which two cylindrical landmarks predict the location of food. The scientific results of that experiment describe some of the capabilities of the apparatus of the present invention. The rat hippocampus experiment was published in the *Journal of Neuroscience*, Vol. 16, pp. 823–835 (1996) and is incorporated herein by reference. The text of that article is not repeated here in the interest of brevity.

In the preferred embodiment shown in FIGS. 1–3, each guide cannula in the array 20 is made of 30 gauge, stainless steel and the array is held together with heat shrink tubing, the lower ends of which remain above the brain surface. The upper ends of the guide cannula preferably form a circle (FIG. 2) and form the base of an inverted cone. The drive nuts 76 are made of stainless steel and are coupled by a molded plastic bridge 80 to 23 gauge drive cannula such as 71 so that, when the screws were turned, drive cannula was driven over the inclined portion of the 30 gauge guide cannula 21a. The tetrode assembly 51 is inserted into the drive cannula 71 so that the tetrode tip 51b just protrudes from the bottom of the corresponding guide cannula 21b. The tetrode 51 is glued to drive cannula 71 at its top end 51a only. A full turn of the drive screw advances the drive cannula and tetrode 320 microns. The tip of the tetrode 51b is thereby advanced through the brain while the guide cannula 21 and drive cannula 71 prevent the portion of the electrode 51 outside the brain from buckling. The total available travel distance in the preferred embodiment for each electrode lower tip is 5–7 mm (shown in phantom in FIG. 1). The 14 tetrodes emerging from the lower portion of the guide cannula array 20 extend in a parallel generally hexagonal lattice with an inter-probe spacing of approximately 250 micrometers. Two of the 14 tetrodes 120 and 121 serve as reference and/or electroencephalograph (EEG) electrodes. The four wires of each of the other twelve tetrodes were connected to separate channels of a multipin connector mounted on headstage prined circuit board 115. The wiring connections are not shown for clarity. A ground lead was connected to a jeweler's screw placed in the skull.

The implantation of the apparatus 10 is accomplished by procedures following NIH guidelines for the use of vertebrate animals. Under sodium pentobarbital anesthesia, the rats were placed in a stereotaxic frame and implanted with the microdrive assembly 10 of the present invention, positioned over the dorsal hippocampus of the right hemisphere. After removal of the dura, the tip of the guide-tube array was placed on the brain surface so that subsequent rotation of the drive screws would advance the tetrode probes into the brain, leaving the lower tips of the guide cannula on the surface of the brain. The craniotomy surrounding the tube array was filled with melted bone wax to protect the brain and the tetrodes from the dental cement 6 (FIG. 1), which anchored the assembly to small stainless steel screws (not shown) placed in the skull. FIG. 1 shows the dental cement 6 anchoring the assembly 10 to the skull 9. The stereotaxic coordinates for the placement of the electrode array were 2.5 mm lateral and 3.8 mm posterior from Bregma. Over a period of approximately one week following surgery, the tetrodes were gradually lowered to the CA1 layer of the dorsal hippocampus.

The invention is capable of being used to study virtually all animal and human brain functions, and is not limited to use in conscious, freely moving subjects. Future applications include a variety of diagnostic uses for humans and animals.

It is to be understood that the array of 14 separate guide and drive cannula may be increased in number and the specific arrangement in the core may be varied with the primary goal being to assure independent adjustability of each of the drive cannula in the array. It is also within the scope of this invention to provide guide means for the electrodes other than the guide cannulae shown. It is also to be understood that, although the drawings show the guide cannula bent and inclined at a 30° angle relative to the vertical, the tubes could also be bent into curved patterns, provided that the lower ends of the guide cannula are aligned in parallel fashion and are closely adjacent each other and that the upper ends are inclined away from the vertical and spaced sufficiently apart from each other to allow for their independent adjustability.

Recording electronics include two unity-gain, miniature, 25 channel FET-preamplifiers and are attached to a connector pin array on headstage printed circuit board 115 on top of the drive assembly. A multiwire cable (not shown) connects the preamplifiers to a 64 channel commutator mounted in the ceiling of the recording room. From the commutator, the signal was directed to seven, custom-designed, 8-channel amplifier modules, with digitally programmable gain and filter settings. Each amplifier module processed data from two tetrodes and transmitted the corresponding signals to a dedicated 80486 microprocessor-based computer. Each computer was equipped with an A/D converter capable of 32 KHz per channel sampling frequency, data acquisition software, and a programmable 10 KHz timestamp clock. One computer served as a master system which synchronized the time-stamp clocks of the six other computers via a parallel 8 bit command cable. A voltage threshold was set independently for each tetrode channel. When the threshold was exceeded on any of the channels, a 1 msec sample of data (32 points/channel), beginning ¼ msec before the threshold crossing, was collected from all four channels and stored on disk.

The position and head orientation of the animal was monitored by tracking two clusters of infrared diodes mounted on the front and rear of a 17 cm, lightweight, aluminum rod attached to the headstage. The front diodes generated a larger light spot than the back diodes, thus permitting the software to discriminate front from back. The video tracking system registered the X,Y coordinates of the two sets of diodes with a sampling frequency of 20 Hz and an effective pixel resolution of approximately 1.5 cm. The total tracking error was estimated to be about 5 cm, in part because of tilt error due to the height of the diode array above the rat's head. The location of the front diode array was taken as the rat's location.

What is claimed is:

1. An apparatus for use in neurophysiological research and clinical diagnosis comprising:

an array of elongated guide cannulae, each of said cannulae having an upper and lower end, said lower ends of said cannulae being aligned parallel with and adjacent each other, said upper ends of said cannulae being inclined outwardly, support means for supporting said array of guide cannulae, wherein said support means includes a core having an upper end and a lower end, a first passageway formed in the lower end of said core, and adapted to receive the lower ends of said array of guide cannulae, a plurality of inclined passageways formed in the upper part of said core, each of said plurality of passageways communicating with said first passageway and extending upwardly and angularly with respect to said first passageway, each of said inclined passageways adapted to carry the upper portion of one of said guide cannulae, at least one electrode slidably carried within each of said guide cannulae, each of said electrodes having upper and lower ends, electrode adjustment means connected to the upper end of said electrodes, said electrode adjustment means moving the electrode or electrodes in each of said guide cannulae independently of the electrodes carried in the other guide cannulae.

2. An apparatus for use in neurophysiological research and clinical diagnosis comprising:

an array of elongated guide cannulae, each of said cannulae having an upper and lower end, said lower ends of said cannulae being aligned parallel with and adjacent each other, said upper ends of said cannulae being inclined outwardly, support means for supporting said array of guide cannulae, at least one electrode slidably carried within each of said guide cannulae, each of said electrodes having upper and lower ends, electrode adjustment means connected to the upper end of said electrodes, said electrode adjustment means moving the electrode or electrodes in each of said guide cannulae independently of the electrodes carried in the other guide cannulae, said electrode adjustment means including a plurality of drive cannulae, one of which is slidably mounted over the upper end of each of said guide cannulae, each of said drive cannulae being connected to the upper end of said electrode or electrodes carried in each respective guide cannulae, a plurality of adjustment rods individually mounted parallel to each of said drive cannulae, and an electrode drive means carried by each of said adjustment rods and connected to one of said drive cannulae such that actuation of an electrode drive means causes sliding motion of one of said drive cannula and the electrode or electrodes to which said drive cannula is connected relative to a guide cannula.

3. The apparatus of claim 2 wherein each of said electrode drive means comprises a hollow nut carried by one of said adjustment rods, and wherein said hollow nut has a turning slot therein.

4. The apparatus of claim 3 further comprising an electrode adjustment tool comprising a drive tip for engaging said turning slot and a turning knob for rotating said drive tip for independent adjustment of each of said drive cannulae.

5. The apparatus of claim 1 wherein said array includes fourteen guide cannulae, twelve of said guide cannulae each carrying four electrodes, one of said guide cannulae carries a reference electrode and one of said guide cannulae carries an electroencephalograph electrode.

6. The apparatus of claim 1 further comprising:

a shroud enclosing said support means and said electrode adjustment means, and a removable cover enclosing the top of the apparatus.

7. The apparatus of claim 1 wherein said core is plastic.

* * * * *